(12) United States Patent
Park et al.

(10) Patent No.: US 8,212,042 B2
(45) Date of Patent: Jul. 3, 2012

(54) QUINOLINE COMPOUND, AND COMPOSITION CONTAINING CENTIPEDE EXTRACT OR COMPOUNDS ISOLATED THEREFROM FOR PREVENTION AND TREATMENT OF CARDIOVASCULAR DISEASE

(75) Inventors: Ho Yong Park, Daejion (KR); Tae-Sook Jeong, Daejeon (KR); Hyun-Woo Oh, Daejeon (KR); Woo-Song Lee, Daejeon (KR); Doo-Sang Park, Daejeon (KR); Jong-Min Han, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 533 days.

(21) Appl. No.: 12/084,467

(22) PCT Filed: May 19, 2006

(86) PCT No.: PCT/KR2006/001889
§ 371 (c)(1),
(2), (4) Date: May 1, 2008

(87) PCT Pub. No.: WO2007/073021
PCT Pub. Date: Jun. 28, 2007

(65) Prior Publication Data
US 2009/0247758 A1   Oct. 1, 2009

(30) Foreign Application Priority Data
Nov. 17, 2005   (KR) ........................ 10-2005-0110261

(51) Int. Cl.
*C07D 215/24* (2006.01)
(52) U.S. Cl. ........................................ 546/155
(58) Field of Classification Search ........................ None
See application file for complete search history.

(56) References Cited

U.S. PATENT DOCUMENTS
5,824,689 A   10/1998   Lee et al.

OTHER PUBLICATIONS

Johan Frostegard, Autoimmunity, Oxidized LDL and Cardiovascular Disease, 1(4) Autoimmunity Revs. 233-37 (Aug. 2002).*
Richard B. Silverman, The Organic Chemistry of Drug Design and Drug Action, Academic Press, p. 5-51 (1992).*
Moon et al., "Jineol, a Cytotoxic Alkaloid from the Centipede *Scolopendra subspinipes*," *J. Nat. Prod.* 59(8):777-779, 1996.
Noda et al., "A Novel Quinoline Alkaloid Possessing a 7-Benzyl Group from the Centipede, *Scolopendra subspinipes*," 49(7):930-931, 2001.
Kim et al., "Structural Characterization of a New Antibiotic Substance Purified from *Scolopendra subspinipes Multilans* L. Koch," *Journal of the Korean Chemical Society* 42(2):236-239, 1998.
Yoon et al., "Antioxidant Effects of Quinoline Alkaloids and 2,4-Di-*tert*-butylphenol Isolated from *Scolopendra subspinipes*," *Biol. Pharm. Bull.* 29(4):735-739, 2006.
International Search Report from International Application No. PCT/KR2006/001889 (Publication No. WO 2007/073021), dated Aug. 22, 2006.

* cited by examiner

*Primary Examiner* — Janet Andres
*Assistant Examiner* — Timothy R Rozof
(74) *Attorney, Agent, or Firm* — Klarquist Sparkman, LLP

(57) ABSTRACT

The present invention relates to a composition for the prevention and treatment of cardiovascular diseases containing the novel quinoline compound, the centipede extracts or compounds isolated from the extracts. The novel quinoline compound, the centipede extracts or a quinoline compound and a phenol compound isolated from the extracts of the invention exhibit excellent LDL-antioxidant activity, ACAT inhibiting activity, and anti-inflammatory activities, so that they can be included as an effective ingredient in a composition for the prevention and treatment of cardiovascular disease including hyperlipidemia, atherosclerosis, coronary heart disease, and myocardial infarction mediated by LDL-oxidation, cholesteryl ester synthesis and accumulation, and inflammation.

8 Claims, 1 Drawing Sheet

QUINOLINE COMPOUND, AND COMPOSITION CONTAINING CENTIPEDE EXTRACT OR COMPOUNDS ISOLATED THEREFROM FOR PREVENTION AND TREATMENT OF CARDIOVASCULAR DISEASE

TECHNICAL FIELD

The present invention relates to a novel quinoline compound and a composition for the prevention and treatment of cardiovascular diseases containing the centipede extracts or compounds isolated therefrom.

BACKGROUND ART

Recently vascular disorder including atherosclerosis is rising with the increase of adult diseases. One of the representative diseases of vascular disorder is atherosclerosis, which is the hardening of artery, in relation with lipid metabolism, attributed to various environmental causes such as dietary habits, smoking, lack of exercise, etc. and mostly developed in cerebral artery or coronary artery and further progressed to circulatory system disease such as heart disease and cerebrovascular disease. For instance, cerebral atherosclerosis shows such symptoms as headache, dizziness or mental disorder and might be progressed to encephalomalacia. Coronary atherosclerosis causes a pain in the heart and arrhythmia, which might be responsible for angina pectoris and myocardial infarction. Atherosclerosis also causes hypertension, heart disease, and apoplexy, etc, and thus atherosclerosis related diseases particularly become one of leading causes of death among men at the age of 50-60s in modern society.

The primary outbreak of atherosclerosis is outlined by 'response-to-injury hypothesis' containing the explanation on chronic inflammation on the damage on blood vessel wall [New Engl. J. Med. 1999, 340, 115-126]. That is, the lost of homeostasis and mal-functioning in vascular endothelial cells, which are attributed to genetic variation, peroxides, hypertension, diabetes, the increase of plasma homocysteine content or/and microorganism infection, result in arteriosclerosis.

More precisely, by the above reasons, low-density lipoprotein (LDL) is converted into highly-modified LDL (HM-LDL) through oxidation, glycosylation, integration, glycoprotein binding, etc, resulting in the stimulation and damage on vascular endothelial cells and smooth, muscle. Subsequently, the expression of vascular cell adhesion molecule-1 (VCAM-1) and release of inflammatory mediator of inflammatory cells in endothelial cells are accelerated, by which LDL flows in and is accumulated in endothelial cells. The accumulated LDL and oxidized HM-LDL promote the inflow and activation of immune cells such as macrophages and T-lymphocytes, resulting in the continuous inflammatory reaction on lesions. Then, the in-coming macrophages or lymphocytes release a hydrolase, an inflammatory mediator and a growth factor, which would destroy the lesion. Then, monocytes flow in and smooth muscle cells are migrated and differentiated and fibrous lesions are generated in the necrotized lesion area. Through the repeated procedure above, the lesions are developed into the fibrous plaque with complicated structure in which necrotizing tissue containing HM-LDL is covered with fibers. Macrophage secretion of matrix metalloproteinases and neovascularization contribute to weakening of the fibrous plaque. Plaque rupture exposes blood components to tissue factor, initiating coagulation, the recruitment of platelets, and the formation of a thrombus. The thrombus and artery hardening lead to the cardiovascular disease including vascular insufficiency.

LDL oxidation is believed to be the most responsible primary cause of arteriosclerosis including atherosclerosis [Circulation, 1995, 91, 2488-2496; Arterioscler. Thromb. Vasc. Biol., 1997, 17, 3338-3346]. Oxidative stress generated in vivo or ex vivo converts LDL into oxidized-LDL. Monocytes attach to endothelial cells that have been induced to express cell adhesion molecules by oxidized-LDL and inflammatory cytokines. Adherent monocytes migrate into the subendothelial space and differentiate into macrophages Uptake of oxidized LDL via scavenger receptors leads to foam cells, resulting in the generation of fatty streak which is the primary lesion of atherosclerosis. The primary lesion of atherosclerosis is characterized by the expressions of adhesion molecules VCAM-1, ICAM-1 (intracellular adhesion molecule-1) and MCP-1 (monocyte chemoattractant protein-1), which are generated in arterial endothelial cells. The expressions of such adhesion molecules are induced by NF-κB (nuclear factor-κB), a transcription factor. NF-κB also causes plaque formation and rupture on blood vessel. NF-κB is activated by various factors including reactive oxygen species (ROS) and cytokine, and is a hetero dimmer composed of p50 and p65 which is included in cells as a transcription factor to regulate many types of target genes. The activated NF-κB is linked to a specific promoter gene to regulate the expression of various inflammatory factors such as IL-1, VCAM-1, ICAM-1 and other factors involved in the progress of atherosclerosis.

It has been reported that antioxidants and radical scavengers inhibit NF-κB activity. Thus, it is expected that an antioxidant inhibits LDL oxidation and adhesion molecule expression, decrease NF-κB activity and thereby arrests atherosclerosis in vivo. And to confirm the expectation, studies have been going (Korean Patent Publication No. 2003-0014155). Besides, studies to find out a LDL peroxide forming factor and eliminate thereof from patients with hyperlipidemia and atherosclerosis [Curr. Atheroscler. Res., 2000, 2, 363-372].

Cytokines are involved in various physiological and pathological processes, and particularly play an important role in immune response, inflammation, tissue reorganization and blastogenesis (Akoum et al., Hum. Reprod. 11:2269-2275, 1996; Inadera et al., Endocrinology 141:50-59, 2000; Xu et al., Life Sci. 64:2451-2462, 1999). Among many cytokines, IL-1α, IL-1β, IL-6, TNFα, and IFNγ are deeply involved in infection or tissue wound (Akoum et al., Hum. Reprod. 11:2269-2275, 1996; Danforth and Sgagias, J. Endocrinol. 138:517-528, 1993; Deshpande et al., Am. J. Reprod. Immunol. 38:46-5, 1997). These cytokines act as intracellular pyrogens and have been also called as inflammatory cytokines (Angele et al., J. Physiol. 277:C35-42, 1999; Bradley and Timothy, Environ. Toxicol. and Chem. 17:3-14, 1998; D'Agostino et al., Ann. N.Y. Acad. Sci. 876:426-429, 1999; Galien and Garcia, Nucleic Acids Res. 25:2424-2429, 1997).

Nitric Oxide (NO) is one of products by inflammatory cytokine in immune system. NO is normally secreted in mammaria, which plays an important role in vascular tone regulation, platelet function, neurotransmission and host defense mechanism (Zancan et al., Endocrinology 140:2004-2009, 1999). In general, only a small amount of NO is generated in some cells (endothelial cells, neurons) but $Ca^+$-independent NO synthase is induced by lipopolysaccharide (LPS) in many kinds of cells such as macrophages, neutrophils, Kupffer's cells and stem cells (Marletta et al., Biochemistry, 27:8706-8711, 1988; McCall et al., Br. J. Pharmacol., 102: 234-238, 1991; Curran et al., J. Exp. Med., 170: 1769-1774, 1989), in particular significant amount of inducible NO synthase (iNOS) is detected in macrophages (Hiki et al., Jpn. J. Pharmacol., 56: 217-220, 1992; Lowenstein et al., Proc. Natl. Acad. Sci. USA 90:9730-9734, 1993).

Macrophages are very important factor which plays an important role in host defense mechanism by engulfing various tumor cells or microorganisms or inhibiting the proliferation thereof when they are activated by foreign substances. It is reported that NO is involved in cell lysis of macrophages (Hibbs et al., Science, 235, 473-476, 1987). When macrophages are activated by such cytokine as IL-1α or LPS, they lead the expression of iNOS and then the iNOS catalytes NO synthesis from L-arginine and oxygen molecules (Palmer et al., Nature 333:664-666, 1988; Karupiah et al., Science 261: 1445-1448, 1993; Kleemann et al., FEBS Lett. 328:9-12, 1993; Wong et al., Adv. Pharmacol. 34: 155-170, 1995). Macrophages also promote T-cell immune response by antigen-presenting and generating cytokine like IL-1α. In addition to normal immune response, iNOS and IL-1α induce inflammatory reaction when they are over-expressed, indicating that regulation of gene expression is a crucial factor to control immune or inflammatory reaction (Wong et al., Adv. Pharmacol. 34: 155-170, 1995; Evans, Agents Actions Suppl. 47: 107-116, 1995; Vane et al., 1994; Moilanen et al., Am. J. Pathol. 150: 881-887, 1995).

The regulation of gene expression by the inflammatory cytokine is mostly conducted during the transcriptional stage of the gene. Particularly, the expression is regulated by the DNA-binding protein such as a transcription factor which recognizes and interacts with the promoter and enhancer element of a gene (Nill et al., J. Immunol. 154:68-79, 1995). It has been known that four transcription factors 'CREB, AP-1, NF-IL6 and NF-kB' are involved in transcriptional regulation of the inflammatory cytokine (Cippitelli et al., J. Biol. Chem. 270: 12548-12556, 1995; Dendorfer, Organs 20:437-44, 1996; Geist et al., Am. J. Reapir Cell. Mol. Biol. 16: 31-37, 1997; Shenkar and Abraham, Am. J. Reapir Cell. Mol. Biol. 14:198-206, 1996; Xie et al., J. Biol. Chem. 269:4705-4708, 1994). Specifically, the expressions of iNOS and IL-1α are known to be regulated by the extent of NF-KB activity (Xie et al., J. Biol. Chem. 269:4705-4708, 1994).

Another responsible factor for coronary heart disease is high blood cholesterol. So, it is important to lower the level of blood cholesterol by dietary treatment reducing cholesterol and lipid intake or by inhibiting cholesterol absorption by suppressing lipid metabolism-related enzymes. To this end, studies on acyl-CoA:cholesterol acyltransferase (ACAT) which is an enzyme responsible for cholesterol esterification have been undergoing.

ACAT is functioning largely in the intestines, the liver and blood vessel wall cells.

First, ACAT esterifies cholesterol in the liver and promotes the absorption thereof. Second, cholesterol, either taken in or synthesized in vivo, is accumulated in very low-density lipoprotein (VLDL), a carrier, in the liver, and then migrated to each organ through blood vessels. At this time, the accumulation of cholesterol in the carrier is made possible by the esterification of cholesterol that is cholesterol is converted into cholesteryl ester. Third, ACAT converts cholesterol into cholesteryl ester in arterial vessel wall forming cells to promote the accumulation of intracellular cholesterol, which is a direct cause of atherosclerosis. By the activation of ACAT, foam cells are subject to contain high level of cholesteryl ester converted from cholesterol. Thus, foam cell formation in macrophages and smooth muscle cells is very important in clinical and experimental aspects. The foam cell proliferation in the vessel wall is closely related to the activation of ACAT, making an ACAT inhibitor as a promising candidate for an effective anti-atherosclerotic agent.

Therefore, it is expected for an ACAT inhibitor firstly to reduce the cholesterol level by inhibiting the absorption of cholesterol in the intestines, secondly to lower the blood cholesterol level by inhibiting the release of cholesterol, migrated from the liver, in blood vessels and thirdly to prevent directly atherosclerosis by preventing the accumulation of cholesterol in the vessel wall.

ACAT inhibitors known so far are inhibitors of mouse liver microsomal ACAT or mouse macrophages (J774) ACAT. Human ACAT was found to be present as two isoforms, ACAT-1 (50 kDa) and ACAT-2 (46 kDa). ACAT-1 is found primarily in the Kupffer cells of the liver, adrenal cortical cells, macrophages, and kidney, while ACAT-2 is mainly located in hepatocytes and intestinal mucosal cells [Rudel, L. L. et al., Curr. Opin. Lipidol. 12, 121-127, 2001]. The human ACAT inhibitors inhibits the absorption of cholesterol taken from food and accumulation of cholesteryl ester in the vessel wall, making it a successful candidate for a preventive and therapeutic agent for hypercholesterolemia, cholesterol gallstone, or atherosclerosis [Buhman, K. K. et al., Nature Med. 6, 1341-1347, 2000].

Recent hyperlipidemia therapeutic agents such as probucol, N,N'-Diphenylenediamine, butylated hydroxy anisol (BHA) and butylated hydroxy toluene (BHT), phenol synthetic antioxidants, have excellent antioxidant activity, so that they reduce the level of LDL cholesterol, arrest oxidation and reduce lesion development but have side effects too.

To prevent such diseases without side effects, an attempt has been made to reduce the level of LDL by inhibiting the absorption and synthesis of cholesterol [Principles in Biochemistry, lipid biosynthesis, 770-817, 3rd Edition, 2000 Worth Publishers, New York; Steinberg, N. Engl. J. Med., 1989, 320, 915-924]. Accordingly, the possibility of combined treatment of LDL-antioxidant and lipid lowering agent has been a major concern to treat patients with hyperlipidemia or atherosclerosis.

The centipede has been utilized as a medicinal animal. And, a method for isolating and purifying a thrombolytic enzyme from large centipede (*Scolopendra subspinipes multilans*) is described in Korean Patent No. 124438. Compounds isolated from the centipede are 3,8-dihydroxyquinoline [Moon, et al., J. Nat. Prod. 59: 777-779, 1996], 2-hydroxy-7-[(4-hydroxy-3-methoxyphenyl)methyl]-3-methoxy-8-quinolyl sulfate [Noda, et al., Chem. Pharm. Bull. 49(7): 930-931, 2001], and 8-hydroxy-1H-2-benzopyran-1-one [Kim, et al., J. Korean Chem. Soc. 42: 236-239, 1998]. However, there has been no report, yet, on the results of study on antioxidant effect or cholesterol metabolism associated activity of the centipede and utilization of the centipede as a cardiovascular disease treating agent.

In the course of searching for a preventive and therapeutic agent for cardiovascular diseases including hyperlipidemia, atherosclerosis, coronary heart disease, and myocardial infarction from natural substances, the present inventors found out that the centipede extracts and quinoline and phenol compounds isolated therefrom exhibit excellent LDL-antioxidant, ACAT inhibitory, and anti-inflammatory activity. And further, the present inventors completed this invention by confirming that the above centipede extracts and compounds isolated from the same can be effectively used for the prevention and treatment of cardiovascular diseases such as hyperlipidemia, atherosclerosis, coronary heart disease, and myocardial infarction.

DISCLOSURE

Technical Problem

It is an object of the present invention to provide a novel quinoline compound.

It is another object of the present invention to provide a preparation method of the novel quinoline compound.

It is a further object of the present invention to provide a composition for the prevention and treatment of cardiovascular disease containing the centipede extracts or quinoline or phenol compounds isolated therefrom.

Technical Solution

To achieve the above objects, the present invention provides a novel quinoline compound.

The present invention also provides a preparation method of the novel quinoline compound.

The present invention further provides a composition for the prevention and treatment of cardiovascular disease containing the centipede extracts or quinoline or phenol compounds isolated therefrom.

Hereinafter, the present invention is described in detail.

The present invention provides a novel quinoline compound represented by the following Formula 1.

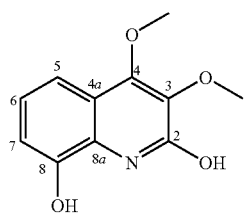

[Formula 1]

The quinoline compound represented by Formula 1 is 3,4-dimethoxy-quinoline-2,8-diol, which can be utilized in the form of a pharmaceutically acceptable salt and at this time it can include any salt, hydrate and solvate produced by the conventional methods.

The present invention also provides a preparation method of the quinoline compound represented by Formula 1 comprising the following steps:

(a) Preparing centipede extracts from the dried centipede by using a solvent;

(b) Preparing chloroform soluble extracts from the extracts suspended in water by serial fractionating with n-hexane, chloroform, and ethylacetate; and (c) Preparing a quinoline compound by isolating and purifying the chloroform soluble extracts with column chromatography.

In step (a), the centipede extracts are prepared by extracting dried centipede with a solvent.

The centipede (*Scolopendra subspinipes mutilans* L. Koch; Scolopendridae) is a dried body of a rare-thorned large centipede, one of Arthropoda, and is also called as Wu Gong. The back of it is green and the abdomen is yellow. The head and legs are red. The male is bigger and the female is thinner and yellow. It is flat, slim and long (14~16 cm in length and 0.6~1 cm in width). It smells fishy and tastes bitter and a little bit salty. The centipede has been utilized as a traditional Chinese and Korean medicine. Large centipedes (*Scolopendra subspinipes*) and blue centipedes are collected in April-June or in August and dried with hanging on bamboo cane or under sunshine after dipping their heads in boiling water. The heads and legs are eliminated and the bodies are chopped. The centipede has also been used as a folk medicine for infantile convulsion, pleurisy and snake biting. According to the pharmaceutical literature classic 'Hyangyakjipseongbang', the centipede has a bitter taste, warm property and venomous, eliminates three parasites (roundworm, mosquito larvae, and pin worm) and regulates ague, alienation and algor.

In this invention, the centipede was purchased from a market or directly collected.

The dried centipede was extracted with a solvent selected from a group consisting of water, C1~C6 alcohol, C5~C7 alkane, chloroform, ethyl acetate, acetone, ether, benzene, methylene chloride, cyclohexane, petroleum ether or a mixture thereof and more preferably a solvent selected from a group consisting of water, C1~C6 alcohol, n-hexane, chloroform, ethyl acetate, acetone or a mixture thereof and most preferably ethanol solvent or acetone solvent.

The amount of the extraction solvent is preferably 1~20 fold the weight of the dried centipede. Any conventional extraction method can be used but hot water extraction at 40~120° C. or ethanol or acetone extraction is preferred. In the case of using ethanol or acetone as a solvent, the centipede has to be dipped in the solvent for 1~5 days at room temperature. The centipede extracts are finally obtained by filtration using a filter paper, purification, and concentration.

Next in step (b), the centipede extracts obtained in step (a), precisely the ethanol extracts, are suspended in water, which are fractionated with n-hexane, chloroform, and ethyl acetate serially. Among those solvent soluble extracts obtained above, the chloroform-soluble phase is taken. Any conventional differential extraction can be used but separatory funnel is preferably used.

In step (c), the chloroform-soluble phase obtained in step (b) is isolated and purified by chromatography to give the novel quinoline compound of Formula 1.

Silica gel column chromatography is performed using such mobile phase as water, chloroform, C1~C4 alcohol, and a mixture thereof, by the conventional method. More preferably, the above C1~C4 alcohol is methanol. Column chromatography is performed once~several times until the purification of the single compound is completed and if necessary, concentration and re-crystallization follow.

More particularly, the chloroform-soluble phase of the centipede ethanol extracts is subjected to silica gel column chromatography with chloroform, methanol or a mixture thereof to give 11 fractions. Among these 11 fractions, the $6^{th}$ fraction (F6) is subjected to silica gel column chromatography using the mixing solvent of chloroform and methanol as a mobile phase, and at this time, the mixing solvent is the mixture of chloroform and methanol at the volume ratio of 20:1. Among fractions obtained from the second column chromatography, the second fraction (F6-2) is subjected to reverse-phase column chromatography using a mixing solvent of methanol and water as a mobile phase to give the quinoline compound represented by Formula 1. At this time, the mixing solvent is preferably prepared by mixing methanol and water at the volume ratio of 55:45.

The quinoline compound represented by Formula 1 prepared above exhibits excellent LDL-antioxidant and ACAT inhibitory activity. Therefore, the compound can be effectively included in a composition for the prevention and treatment of cardiovascular disease including hyperlipidemia, atherosclerosis, coronary heart disease, and myocardial infarction, which have been known to be developed by LDL oxidation or cholesteryl ester synthesis and accumulation.

The present invention further provides a composition for the prevention and treatment of cardiovascular disease containing the centipede extracts.

The centipede extracts of the invention are extracted preferably with such solvent as water, C1~C6 alcohol, C5~C7 alkane, chloroform, ethyl acetate, acetone, ether, benzene, methylene chloride, cyclohexane and petroleum ether or a mixture thereof, more preferably with such solvent as water, C1~C6 alcohol, n-hexane, chloroform, ethyl acetate and acetone or a mixture thereof and most preferably with such solvent as ethanol or acetone. At this time, the preferable amount of the extraction solvent is 1~20 times the dried centipede. Any conventional extraction method can be used but hot water extraction at 40~120° C. or ethanol or acetone extraction is preferred. In the case of using ethanol or acetone as a solvent, the centipede has to be dipped in the solvent for 1~5 days at room temperature. The centipede extracts are finally obtained by filtration using a filter paper, purification, and concentration.

More preferably, the centipede extracts are fractions obtained from column chromatography of the centipede extracts. At this time, the column chromatography is performed by the conventional procedure by using water, chloroform, C1~C4 alcohol or a mixing solvent thereof as a mobile phase. Herein, C1~C4 alcohol is preferably methanol and the mixing solvent is the mixture of chloroform and methanol or the mixture of methanol and water.

The centipede extracts of the present invention not only have an excellent antioxidant activity against LDL and inhibitory effect on the activity of ACAT, an enzyme for esterification of cholesterol but also has functions of anti-inflammation and inhibiting intracellular NO and ROS generation. Thus, the centipede extracts of the invention can be an effective ingredient for a composition for the prevention and treatment of cardiovascular disease such as hyperlipidemia, atherosclerosis, coronary heart disease, and myocardial infarction, induced by LDL oxidation or cholesteryl ester synthesis and accumulation.

The present invention also provides a composition for the prevention and treatment of cardiovascular disease containing the quinoline compound represented by Formula 2 and the phenol compound represented by Formula 3.

The quinoline compound and phenol compound can be purchased from a market or be prepared by the conventional method well-known to those in the art or by the preparation method of the invention which can be modified if necessary. The above compounds are preferably isolated and purified from the centipede.

[Formula 2]

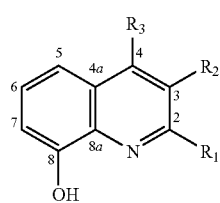

Wherein, R1, R2 and R3 are independently H, OH, or C1~C4 alkoxy.

[Formula 3]

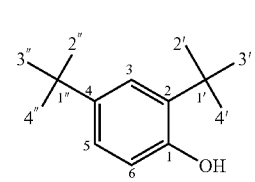

The phenol compound represented by Formula 3 is 2,4-di-tert-butyl-phenol.

The compound represented by Formula 2 is preferably 3,8-dihydroxyquinoline or 3,4-dimethoxyquinoline-2,8-diol.

Each Formula is as shown in Table 1.

TABLE 1

| Compound | Formula |
| --- | --- |
| 1 | 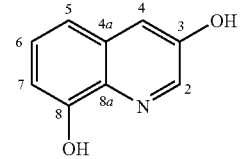 |
| 2 | 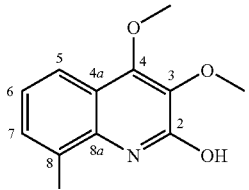 |

The quinoline compound of Formula 2 and the phenol compound of Formula 3 exhibit an excellent antioxidant activity against LDL and inhibitory effect on the activity of ACAT, an enzyme for esterification of cholesterol. Thus, these compounds can be effective ingredients for a composition for the prevention and treatment of cardiovascular disease such as hyperlipidemia, atherosclerosis, coronary heart disease, and myocardial infarction, induced by LDL oxidation or cholesteryl ester synthesis and accumulation.

The composition of the present invention can additionally include, in addition to the novel quinoline compound, the centipede extracts and the quinoline or phenol compound isolated from the extracts, one or more effective ingredients having the same or similar functions.

The composition of the present invention can also include, in addition to the above-mentioned effective ingredients, one or more pharmaceutically acceptable carriers for the administration. A pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each disease or according to ingredients by following a method represented in Remington's Pharmaceutical Science (Mack Publishing Company, Easton Pa., 18th, 1990).

The composition of the present invention can be administered orally or parenterally (for example, intravenous, hypodermic, local or peritoneal injection). The effective dosage of the composition can be determined according to weight, age, gender, health condition, diet, administration frequency, administration method, excretion and severity of a disease. The dosage of the centipede extracts is 10~2,000 mg/kg per day, and preferably 50~500 mg/kg per day. The dosage of the quinoline or phenol compound is 0.01~100 mg/kg per day and preferably 0.05~10 mg/kg per day. Administration frequency is once a day or preferably a few times a day.

The novel quinoline compound, the centipede extracts and the quinoline or phenol compound isolated from the extracts of the present invention were orally administered to mice to investigate toxicity. As a result, they were evaluated to be safe substances since Their estimated $LD_{50}$ values are much greater than 1,000 mg/kg in mice.

The composition of the present invention can be administered singly or treated along with surgical operation, hormone therapy, chemotherapy and biological reaction regulator, to prevent and treat cardiovascular diseases.

The composition of the present invention can be included in health food for the purpose of improving cardiovascular disease. At this time, the novel quinoline compound, the centipede extracts and the quinoline or phenol compound isolated from the extracts of the present invention can be added as it is or after being mixed with other food or ingredients, according to the conventional method. The mixing ratio of effective ingredients is determined by the purpose of use (prevention, health or therapeutic treatment). In the case of producing food or beverages, the novel quinoline compound, the centipede extract and the quinoline or phenol compound isolated from the extract of the present invention is preferably added by 0.01~10 weight %, more preferably 0.05~1 weight %, to the raw material. However, the content of the novel quinoline compound, the centipede extracts and the quinoline or phenol compound isolated from the extract of the present invention might be less than the above when it is administered for long-term to improve health conditions but the effective dosage could contain more than the above amount because the novel quinoline compound, the centipede extracts and the quinoline or phenol compound isolated from the extract of the invention is very safe.

There is no limit in applicable food, which is exemplified by meats, sausages, bread, chocolate, candies, snacks, cookies, pizza, ramyun, noodles, dairy products including ice cream, soups, beverages, tea, drinks, alcoholic drinks and vitamin complex, etc, and in fact every health food generally produced are all included.

Health beverages containing the composition of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. As a sweetener, either natural sweetener such as thaumatin and stevia extract or artificial sweetener such as saccharin and aspartame can be used. The ratio of natural carbohydrate to the composition of the present invention is preferably 0.01~0.04 g to 100 ml, more preferably 0.02~0.03 g to 100 ml.

In addition to the ingredients mentioned above, the composition of the present invention can include in variety of nutrients, vitamines, electrolytes, flavoring agents, coloring agents, pectic acid and its salts, arginic acid and its salts, organic acid, protective colloidal viscosifiers, pH regulators, stabilizers, antiseptics, glycerin, alcohols, carbonators which used to be added to soda, etc. The composition of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.01~0.1 weight part per 100 weight part of the composition of the invention.

DESCRIPTION OF DRAWINGS

The application of the preferred embodiments of the present invention is best understood with reference to the accompanying drawings, wherein.

MODE FOR INVENTION

Figure 1:
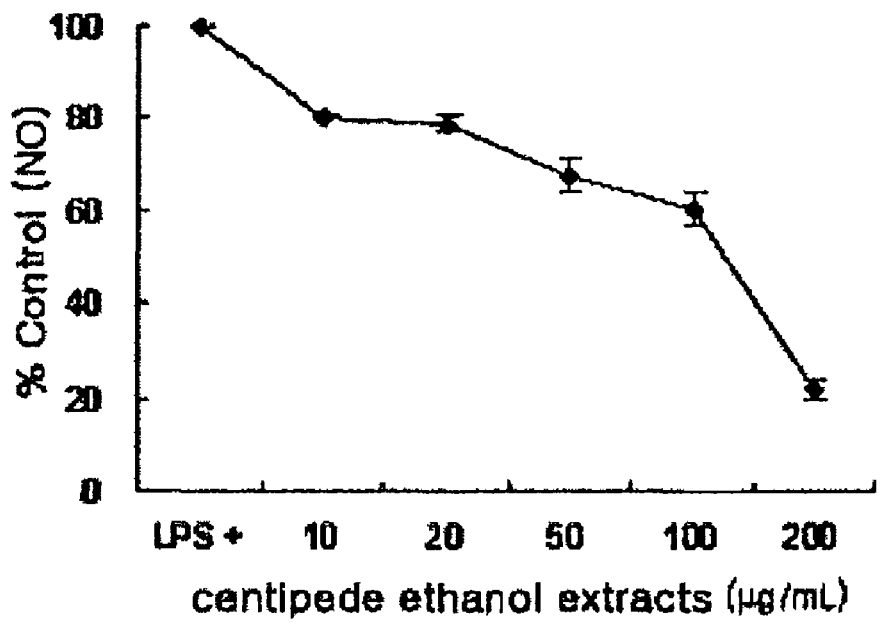
FIG. 1 is a graph illustrating the NO generation inhibitory activity of the centipede ethanol extracts of the invention in LPS-treated macrophages.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of the Centipede Extracts and Quinoline and Phenol Compounds

<1-1> Preparation of the Centipede Extracts

Acetone ($CH_3COCH_3$) or ethanol (700 ml each) was added to 250 g of the dried centipede (*Scolopendra subspinipes mutilans* L. Koch, Daejeon, Korea), which was standing at room temperature for 3 days, followed by extraction. The extracts were filtered with a filter paper to obtain the extracts and solid residue. The obtained extracts were concentrated under reduced-pressure to give 85 g of the oily centipede acetone extracts and 40 g of the oily centipede ethanol extracts.

The centipede acetone extracts and ethanol extracts were tested by the methods described in Experimental Examples 1 and 2. As a result, the two extracts exhibited excellent antioxidant activity against LDL and ACAT activity-inhibitory capacity, and the ethanol extracts with better effect was used in Examples hereinafter.

<1-2> Preparation of a Nonpolar Solvent-Soluble Phase from the Centipede Extract The centipede ethanol extracts prepared in the above Example <1-1> were suspended in 700 ml of water and fractionated serially with n-hexane, chloroform ($CHCl_3$) and ethyl acetate (EtOAc) to obtain 26 g of a n-hexane-soluble phase, 0.7 g of a $CHCl_3$-soluble phase and 1.5 g of an EtOAc-soluble phase.

The soluble phases were tested by the same manner as described in Experimental Examples 1 and 2. As a result, the EtOAc-soluble phase and $CHCl_3$-soluble phase were confirmed to have excellent LDL-antioxidant activity and ACAT-inhibitory effect. Those phases were used in Example <1-3> or <1-4>.

<1-3> Separation of Compounds from the Centipede EtOac-Soluble Phase 1.5 g of EtOAc-soluble phase obtained in Example <1-2> was subjected to column chromatography.

First, the brown solid substance of EtOAc-soluble phase was absorbed to silica gel. Then, silica gel chromatography (φ55×250 mm) was performed with increasing polarity using the mixing solvent of chloroform and methanol (100:0~0:100, V/V) as a mobile phase to give 25 fractions (F1~F10). 25 fractions were tested for LDL-antioxidant and ACAT inhibitory activity by the same manner as described in Experimental Examples 1 and 2. As a result, the fraction 2 (F2) exhibited the highest effect, thereby the fraction was used for the following separation process.

Column chromatography was performed again with the active fraction (F2, 400 mg). Particularly, the second silica gel chromatography (φ23×140 mm) was performed with raising polarity by using the mixing solvent of chloroform and methanol (99:1~1:9, V/V) as a mobile phase to give 16 fractions (F2-1~F2-16). Those 16 fractions were tested for LDL-antioxidant and ACAT inhibitory activity by the same manner as described in Experimental Examples 1 and 2. As a result, the $8^{th}$ fraction (F2-8) exhibited the highest effect, which was further used for the following separation process.

The $8^{th}$ fraction of the fraction 2 (F2-8, 189 mg) was subjected to C18 column chromatography (φ13×115 mm) using the mixing solvent of methanol and water (4:1, V/V) as a mobile phase to give 14 fractions. Among the $2^{nd}$~$6^{th}$ fractions (F-2-8-2~F-2-8-6) showing excellent LDL-antioxidant and ACAT inhibiting activities, the $3^{rd}$~the $5^{th}$ fractions (F-2-8-3~F-2-8-5) were subjected to C18 column chromatography using the mixing solvent of methanol and water (7.5:3.5, V/V) as a mobile phase to give the $3^{rd}$ and the $4^{th}$ fraction (54 mg) showing excellent LDL-antioxidant and ACAT inhibiting activities. Those fractions were subjected to C-18 (ODS) Prep-TCL using the mixing solvent of methanol and water (7:3, V/V) as a mobile phase to give compound 1 (39.3 mg) showing excellent LDL-antioxidant activity.

<1-4> Isolation of a Compound from Chloroform-Soluble Phase Prepared from the Centipede Extracts 0.7 g of chloroform-soluble phase of the centipede extracts obtained in the above Example <1-2> was subjected to column chromatography to isolate the compound of the invention.

The brown solid substance of chloroform-soluble phase was adsorbed to silica gel. Then, silica gel column chromatography (φ52×270 mm) was performed with increasing polarity using the mixing solvent of chloroform and methanol (100:0~1:9, V/V) as a mobile phase to give 11 fractions (F1~F11). 11 fractions were tested for LDL-antioxidant and ACAT inhibitory capacity by the same manner as described in Experimental Examples 1 and 2. As a result, the active fractions, the first (F1) and the $6^{th}$ (F6) were obtained.

The fraction F1 (14 mg) was subjected to C18 Prep-TLC (ODS Prep-TLC) using the mixing solvent of methanol and water (100:1, V/V) as a mobile phase and the active compound 3 was obtained from the first fraction (F1-1, 3 mg).

The second fraction (F6-2) was purified from the fraction F6 (40 mg) by silica Prep-TLC using the mixing solvent of chloroform and methanol (20:1, V/V) as a mobile phase, followed by C18 Prep-HPLC using the mixing solvent of methanol and water (55:45, V/V) as a mobile phase to give compound 2, the $6^{th}$ fraction (F6-2-6, 6 mg).

<1-5> Structural Analysis of Compounds of the Invention

Structural analysis of three compounds obtained in the above Examples <1-3> and <1-4> was performed as follows.

Molecular weight and molecular formula were determined by VG high resolution GC/MS spectrometer (Election Ionization MS, Autospec-Ultima, Micromass, UK) and rotatory power was measured using DIP-181 digital polarimeter (Jasco, Japan). NMR (AMX 500, Bruker, Germany) was carried out to obtain $^1$H NMR, $^{13}$C NMR, HOMO-COSY, NOE (Nuclear Overhauser Exchange), HMQC ($^1$H-Detected heteronuclear Multiple-Quantum Coherence), HMBC (Heteronuclear Multiple-Bond Coherence) and DEPT (Distortionless Enhancement by Polarization) spectra, followed by determination of molecular structure.

The results of the above analysis were compared with literatures reported earlier [Moon, et al., 59: 777-779, 1996; Pouchert, C. J., 1985. The Aldrich library of FT-IR spectra vapor phase Edition 1. Vol. 1, 1088B; Pouchert, C. J., Behnke, J., 1993. The Aldrich library of $^{13}$C and $^1$H NMR spectra edition 1. Vol. 2, 267]. As a result, the compound 1 of the invention was identified as 3,8-dihydroxyquinoline and the compound 2 was identified as 3,4-dimethoxyquinoline-2,8-diol. The compound 3 of the invention was identified as 2,4-di-tert-butylphenol.

[Compound 1] 3,8-dihydroxyquinoline
1) Physical property: Yellow solid
2) Molecular weight: 161
3) Molecular formula: $C_9H_7NO_2$
4) $^1$H NMR (CD$_3$OD, 500 MHz) δ 8.45 (1H, d, J=2.42, H-2), 7.44 (1H, d, J=2.38, H-4), 7.29 (1H, t, J=7.84, H-6), 7.14 (1H, d, J=8.13, H-5), 6.86 (1H, d, J=7.43, H-7).
6) $^{13}$C NMR (CD$_3$OD, 125 MHz) δ 154.2 (C-8), 153.0 (C-3), 142.3 (C-2), 134.9 (C-8a), 131.9 (C-4a), 129.0 (C-6), 117.9 (C-5), 117.2 (C-4), 109.0 (C-7).
7) EI-MS (70 ev); m/z (%): 161(100) [M]$^+$, 133(90), 104 (63), 91(10).

[Compound 2] 3,4-dimethoxyquinoline-2,8-diol
1) Physical Property: Yellow solid
2) Molecular weight: 221
3) Molecular Formula: $C_{11}H_{11}NO_4$
4) $^1$H NMR CD$_3$OD, 500 MHz) δ 7.33 (1H, d, J=8.16, H-5), 7.05 (1H, d, J=8.00, H-6), 6.93 (1H, t, J=7.78, H-7), 4.22 (3H), 3.88 (3H).
6) $^{13}$C NMR (CD$_3$OD, 125 MHz): δ 163.0 (C-2), 155.6 (C-8), 145.2 (C-4), 136.5 (C-8a), 125.6 (C-6), 123.9 (C-3), 119.6 (C-4a), 114.7 (C-5), 114.5 (C-7), 61.4 (—OCH$_3$), 61.2 (—OCH$_3$).
7) EI-MS (70 ev); m/z (%): 221(82) [M]$^+$, 206(100), 192 (17), 178(32), 161(23).

[Compound 3] 2,4-di-tert-butylphenol
1) Physical property: Yellow solid
2) Molecular weight: 206
3) Molecular formula: $C_{14}H_{22}O$
4) $^1$H NMR (CD$_3$OD, 500 MHz) δ 7.28 (1H, d, J=2.1, H-3), 7.05 (1H, dd, J=8.2, 2.2, H-5), 6.57 (1H, d, J=8.2, H-6), 4.58 (1H, s, —OH), 1.40 (9H, s, H-2', 3', 4'), 1.28 (9H, s, H-2", 3", 4")
6) $^{13}$C NMR (CD$_3$OD, 125 MHz): 153.5 (C-1), 143.7 (C-4), 135.9 (C-2), 124.8 (C-3), 124.2 (C-5), 116.6 (C-6), 35.4 (C-1"), 35.0 (C-1'), 32.3 (C-2"), 32.3 (C-3"), 32.3 (C-4"), 30.4 (C-2'), 30.4 (C-3'), 30.4 (C-4').
7) EIMS (rel. int.) m/z: EI-MS (70 ev) m/z: 206(16) [M]$^+$, 191(100), 149(5), 119(8), 83(8), 69(34), 57(30).

Example 2

Preparation of the Centipede Extracts

To 100 g of the dried centipede was added 1,000 ml of 95% ethanol, followed by extraction at room temperature for 72 hours by the same method as described in Example <1-1>. The extracts were filtered and dried to give the centipede extracts.

Experimental Example 1

Measurement of the LDL-Antioxidant Activities of Compounds of the Present Invention by TBARS (Thiobarbituric Acid Reactive Substances)

The centipede extracts, a quinoline compound and a phenol compound isolated therefrom were tested as follows for the antioxidant activity against LDL-oxidation.

The antioxidant activity was calculated by measuring dialdehyde which is an oxidation product of unsaturated fatty acid produced from $Cu^{2+}$-mediated LDL-oxidation by TBA (thiobarbituric acid) method [Packer, L. Ed., Methods in Enzymology. Vol. 234, Oxygen radicals in biological systems Part D. Academic press, San Diego, 1994].

Three hundred ml of human plasma was taken, followed by centrifugation at 100,000×g for 24 hours with an ultracentrifuge. VLDL/chylomicrom layer floating in the supernatant was eliminated. The specific gravity of the remaining solution was adjusted to 1.063 g/ml, followed by centrifugation at 100,000×g for 24 hours to separate about 25 ml (1.5~2.5 mg protein/ml) of LDL in supernatant. Twenty μl (protein concentration: 50-100 μg/ml) of the LDL isolated from the above was mixed with 210 μl of 10 mM phosphate-buffered saline (PBS), to which 10 μl of each solvent extracts of the invention, each fraction and compound solution were added. At that time, the compounds were dissolved in dimethylsulfoxide (DMSO) and diluted at different concentrations to be ready for the experiment. DMSO alone was used as a negative control. As a positive control, probucol, a known antioxidant, was added. To each solution was added 10 μl of 0.25 mM $CuSO_4$, followed by reaction at 37° C. for 4 hours. The reaction was terminated by addition of 1 ml of 20% trichloroacetic acid (TCA) solution. 1 ml of 0.67% TBA solution dissolved in 0.05 N NaOH solution was added thereto, followed by stirring for 10 seconds. The solution was heated at 95° C. for 5 minutes to induce color development and then cooled down with ice water. The solution was centrifuged at 3000 rpm for 5 minutes to separate the supernatant and $OD_{540}$ was measured with UV/VIS spectrophotometer to measure the level of malondialdehyde (MDA) generated by the color development.

In the meantime, to calculate the standard curve of malondialdehyde, the stock solution of malonaldehyde bis (dimethylacetal) was diluted, resulting in PBS standard solution containing 0~10 nmol malondialdehyde. Color development was also induced in each 250 μl of PBS standard solution to measure $OD_{540}$ to determine the malondialdehyde standard curve. The malondialdehyde generated from the compounds of the invention was quantified and inhibitory activity and $IC_{50}$ were also calculated.

The results are shown in Table 2.

TABLE 2

| Samples | Inhibitory activity (%) or $IC_{50}$ (μM) |
|---|---|
| Centipede acetone extracts (40 μg/ml) | 73% inhibition |
| Centipede ethanol extracts (40 μg/ml) | 80% inhibition |
| n-hexane-soluble phase (20 μg/ml) | 35% inhibition |

TABLE 2-continued

| Samples | Inhibitory activity (%) or $IC_{50}$ (μM) |
|---|---|
| Chloroform-soluble phase (20 μg/ml) | 85% inhibition |
| EtOAc-soluble phase (20 μg/ml) | 98% inhibition |
| Compound 1 | 2.6 μM |
| Compound 2 | 63 μM |
| Compound 3 | 8.2 μM |
| Positive control (Probucol) | 3.1 μM |

As shown in Table 1, the centipede acetone extracts obtained in Example <1-1> exhibited 73% antioxidant effect at the concentration of 40 μg/ml, whereas the centipede ethanol extracts showed 80% antioxidant effect at the same concentration, suggesting that both extracts have excellent antioxidant activities.

In the meantime, ethyl acetate-soluble phase exhibited 98% antioxidant activity against LDL-oxidation at the concentration of 20 μg/ml, indicating that the phase has the highest antioxidant activity among solvent-extractable phases including n-hexane-soluble and chloroform-soluble phases.

The antioxidant activities of compound 1, 3,8-dihydroxyquinoline, obtained in Example <1-2>, compound 2, 3,4-dimethoxyquinoline-2,8-diol, and compound 3, 2,4-di-tert-butylphenol were tested, resulting in $IC_{50}$ was 2.6 μM, 63 μM, and 8.2 μM, respectively. Particularly, the compound 1 exhibited lower $IC_{50}$ than that of a positive control, indicating that the compound 1 has excellent LDL-antioxidant activity. The compound 2 showed higher $IC_{50}$ than that of a positive control, but still exhibited LDL-antioxidant activity. And the compound 3 had also excellent LDL-antioxidant activity even though it showed higher $IC_{50}$ than that of a positive control.

Therefore, the centipede extracts of the present invention, a quinoline compound and a phenol compound isolated therefrom have been confirmed to be effective ingredient for the composition of the invention for the prevention and treatment of LDL-oxidation mediated cardiovascular diseases including hyperlipidemia or atherosclerosis.

Experimental Example 2

Effect of the Extracts and Compounds of the Present Invention on ACAT Activity

To investigate the ACAT inhibitory activity of the centipede extracts, a quinoline compound and a phenol compound isolated therefrom, following experiments were performed.

<2-1> Preparation of ACAT Enzyme

To investigate the effect on human ACAT-1 and ACAT-2 activities, hACAT-1 and hACAT-2 proteins were obtained using baculovirus expression system.

hACAT-1 and hACAT-2 cDNAs, obtained by human liver cDNA library screening, were inserted into the baculovirus transfer vector, which was introduced into an insect cell line sf9 to produce virus. Then, recombinant virus of each hACAT-1 and hACAT-2 was separated by plaque purification, followed by amplification three times to raise titer of the viral stock. Hi5 insect cells having high protein expression efficiency were infected with the recombinant virus (1 multiplicity of infection), followed by shaking culture at 27° C. for a day. Centrifugation was performed at 500×g for 15 minutes to separate microsome fractions from Hi5 cells over-expressing hACAT-1 and hACAT-2. The resultant cells were lysed in a hypotonic buffer by quick freezing-quick thawing, followed by ultracentrifugation at 100,000×g for one hour. The obtained microsome fractions were suspended in the hypotonic buffer until the concentration of the protein reached 8 mg/ml, which was stored in a deep freezer until use.

<2-2> Measurement of ACAT Activity

To measure the ACAT activity, $[1-^{14}C]$ oleoly-CoA (56.0 µCi/µmol; Amersham) was used as a substrate and a method of Brecher & Chan was used with a slight modification [P. Brecher and C. Chan, Biochem. Biophys. Acta, 617, 458, 1980].

Ten µl of the centipede extracts or the compound prepared in the above Example was mixed with 4.0 µl of the microsomal solution prepared in Experimental Example <2-1>, 20.0 µl of an activity analyzing buffer (0.5 M $KH_2PO_4$, 10 mM DTT, pH 7.4; Sigma), 15.01 of fatty acid-free bovine serum albumin (fatty acid-free BSA, stock concentration 40 mg/ml; Sigma), 2.0 µl of cholesterol (stock solution 20 mg/ml; Sigma) and 41.0 µl of distilled water, which was preincubated at 37° C. for 15 minutes. The reaction was initiated by the addition of 8 µl of $[1-^{14}C]$ oleoly-CoA (0.05 µCi, final concentration: 10 µM). After 30 minutes of incubation at 37° C., 1 µl of the mixture of isopropanol and heptane (4:1, v/v) was added to terminate the reaction. A mixture of 600 µl of heptane and 400 µl of 0.1 M $KH_2PO_4$ (pH 7.4) were added thereto, and the mixture was vigorously mixed with a vortexer, followed by centrifugation at 300×g for 5 minutes. One hundred µl of the upper heptane phase obtained by the centrifugation was put in a scintillation bottle, to which 4 ml of scintillation cocktail (Lipoluma) was added. The radioactivity of the mixture was measured with 1450 Microbeta liquid scintillation counter (Wallacoy).

ACAT activity was calculated as pmol of cholesteryl oleate synthesized per 1 mg of protein in one minute (pmol/minute/mg of protein).

The results are shown in Table 3.

TABLE 3

| Samples | Inhibitory activity (%) | |
|---|---|---|
| | hACAT-1 | hACAT-2 |
| Centipede acetone extracts (200 µg/ml) | 53 | 50 |
| Centipede ethanol extracts (200 µg/ml) | 61 | 55 |
| n-Hexane-soluble phase (200 µg/ml) | 28 | 16 |
| Chloroform-soluble phase (200 µg/ml) | 80 | 73 |
| Ethyl acetate-soluble phase (200 µg/ml) | 72 | 69 |
| Compound 1 (100 µg/ml) | 60 | 50 |
| Compound 2 (100 µg/ml) | 79 | 58 |
| Compound 3 (100 µg/ml) | 63 | 51 |

As shown in Table 3, the centipede extracts of the invention, a quinoline compound, and a phenol compound isolated therefrom were proved to have excellent hACAT-1 and hACAT-2 inhibiting activity.

Therefore, the centipede extracts of the invention, a quinoline compound, and a phenol compound isolated therefrom can be included as an effective ingredient of a composition for the prevention and treatment of cardiovascular diseases including hyperlipidemia, atherosclerosis, coronary heart disease, and myocardial infarction mediated by cholesteryl ester synthesis and accumulation.

Experimental Example 3

Cytotoxic Test in Macrophages

<3-1> Cell Culture

RAW264.7 cells (murine macrophage cell line, ATCC) were cultured in DMEM (Gibco) supplemented with 10% FBS (Hyclone), 2 mM L-glutamine, 100 units/ml penicillin and 100 µg/mL streptomycin in a humid 5% $CO_2$ incubator at 37° C.

<3-2> Cytotoxic Test in Macrophages

First, LDH (lactate dehydrogenase) analyzing media for background control (DMEM+1% FBS+antibiotics 1×), low control (DMEM+1% FBS+antibiotics 1×) and high control (DMEM+1% FBS+2% Triton X-100+antibiotics 1×) were prepared. The centipede extracts prepared in Example 2 was inoculated into each low control medium at different concentrations of 1, 5, 10, 20, 50, 100, and 200 µg/ml. DMSO concentration was adjusted to be less than 0.1% in DMEM.

DMEM and $5×10^4$ cells/100 µl of macrophages (RAW 264.7) were placed in each well of a 96 well plate, followed by culture for 24 hours in a $CO_2$ incubator. Those cells were not added into the background control wells. 24 hours later, media were removed from each well, then media for background control, low control and high control assay were added to each well by 200 µl per well, followed by further culture for 72 hours. One hundred µl of supernatant of each well was taken and transferred into a new 96 well plate. One hundred µl of solution C (TAKARA Co., LDH Cytotoxicity Detection Kit) containing diaphorase and $NAD^+$ was add into each well of the plate, followed by reaction for 30 minutes. Then, the optical density at 490 nm ($OD_{490}$) was measured using a microplate reader (Bio-Rad Co., USA).

As a result, every sample exhibited 100% survival rate at 0-200 µg/ml, indicating that all the samples have no cytotoxicity.

Experimental Example 4

Measurement of NO Generated by Macrophages

The present inventors investigated whether the nitric oxide (NO) generation by LPS could be inhibited by the centipede ethanol extracts.

First, $1×10^4$ cells were cultured in a 96 well plate. When the cells were grown up to 80% of each well, the centipede extracts prepared in Example 2 was added with increasing the concentration. The cells were stimulated by 1 µg/mL of LPS for about 16 hours. The supernatant was obtained by precipitation of cells without centrifugation. NO generation was quantified using the supernatant by measuring $NO_2^-$, which is the NO reaction product.

Particularly, 50 µl of culture supernatant and the same amount of Greiss reagent [0.5% sulfanilyamide, 0.05% N-(1-naphthyl)ethylene diamine dihydrochloride/2.5% $H_3PO_4$] were mixed in a 96 well tissue culture plate, which was standing for 10 minutes in the dark at room temperature for reaction. $OD_{540}$ was measured with a microplate reader (Bio-Rad Co., USA). Standard curve of $NO_2^-$ concentration was made based on $NaNO_3$ to quantify NO generation. Every experiment was repeated more than three times, and each was quantified by Dunnet's t-test.

As a result, NO generation in a control treated with 1 µg/mL of LPS was approximately 10 fold increased, whereas NO generation in the centipede extracts treated group was decreased dose-dependently. The Jeju island originated centipede extracts exhibited the highest activity, and thus NO generation inhibiting effect was almost 73% at 200 μg/ml (Table 4 and FIG. 1).

Therefore, it was confirmed that the centipede extracts inhibit NO generation in LPS-induced macrophages, reduce the activity of macrophages and thereby inhibit another inflammation factor or disease out-break.

TABLE 4

| Sample | Inhibition of NO generation (%) |
|---|---|
| Centipede ethanol extracts (200 μg/ml) | 73% inhibition |

Experimental Example 5

Measurement of ROS in Macrophages

To examine reactive oxygen species (ROS) generation inhibiting effect of the centipede extracts in LPS-induced macrophages, the present inventors measured hydroxyl radical using 2',7'-dichlorofluorescein diacetate ($DCFH_2$-DA, Molecular Probes) according to the method of Hayakawa et al (EMBO J. 22, 3356-3366, 2003). $DCFH_2$-DA itself has cytopermeability but not fluorescence. However, once it enters cells, it is decomposed by cellular esterase, resulting in 2'-7'-dichlorodihydrofluorescein ($DCFH_2$), which was then oxidized into fluorescent 2'-7'-dichlorofluorescein (DCF) by peroxidase, cytochrome c and $Fe^{2+}$, etc. DCF suggests the level of $H_2O_2$ and has intracellular peroxidase activity. That is, the level of hydroxyl radical was measured by quantifying intracellular hydroxyl peroxidase accumulated by an external stimulus.

Particularly, $1 \times 10^4$ cells were cultured in a 96 well plate. When 80% of the plate was filled with the growing cells, the centipede extracts prepared in Example 2 was added at different concentration with increasing the concentration. The cells were stimulated with 1 μg/mL of LPS for about 16 hours, followed by reaction for one hour with the addition of 10 μM $DCFH_2$-DA. Upon completion of the reaction, the reactant was washed 5 times with PBS. $OD_{485}$ (excitation) and $OD_{530}$ (emission) were measured by using a fluorescence microplate reader (1420 VICTOR, Perkin-Elmer, Belgium).

Figure 2:
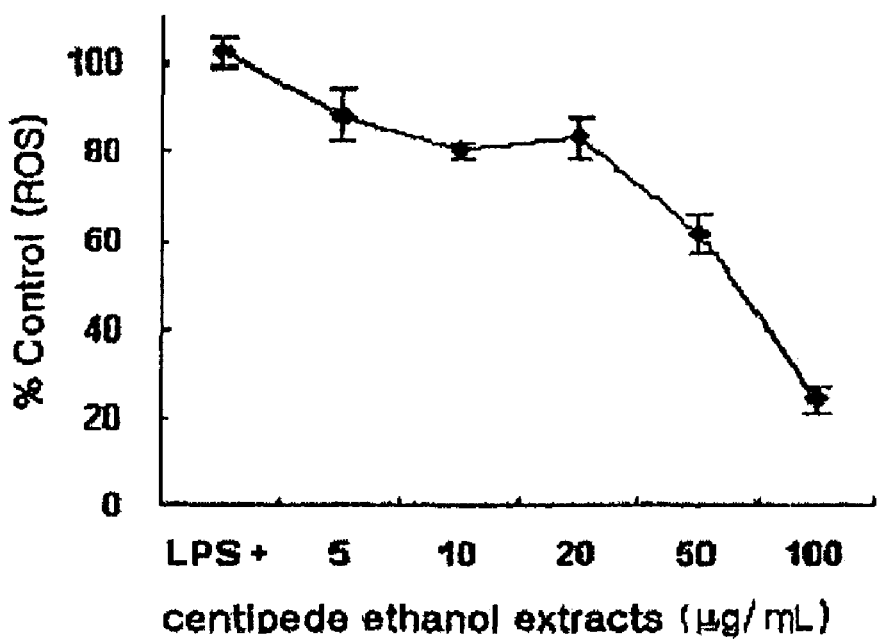
FIG. 2 is a graph illustrating the ROS generation inhibitory activity of the centipede ethanol extracts of the invention in LPS-treated macrophages.

As a result, fluorescence of DCF, an index for ROS, was increased time-dependently in a control treated with LPS alone, while fluorescence of DCF was suppressed by the centipede extracts dose-dependently (Table 5 and FIG. 2).

TABLE 5

| Sample | Inhibition of ROS generation (%) |
|---|---|
| Centipede ethanol extracts (100 μg/ml) | 75% inhibition |

Experimental Example 6

Acute Toxicity of the Centipede Extracts and Compounds of the Present Invention

In order to investigate acute toxicity of the centipede extracts, a quinoline compound, and a phenol compound isolated therefrom, following experiments were performed.

Twelve of each female and male specific pathogens-free ICR mice at 4 weeks old (3 of each female and male/group) were raised in an animal facility where temperature was regulated to 22±3° C., humidity was adjusted to 55±10% and light was also regulated to 12 L/12 D. The animals were adapted for one week before being used. Feed for laboratory animals (CJ Corp., Seoul, Korea, for mouse and rat) and drinking water were provided at any time after being sterilized.

The centipede extracts prepared in the above example or quinoline compound or phenol compound isolated from the same was formulated by 50 mg/ml using 0.5% Tween 80 as a solvent, then orally administered to mice at the concentration of 0.04 ml (100 mg/kg), 0.2 ml (500 mg/kg) and 0.4 ml (1,000 mg/kg) per 20 g of mouse body weight, respectively. Samples were administered orally just once. After the administration, side effects and death were observed for 7 days. Particularly, changes of any symptoms and death of an animal were observed 1 hour, 4 hours, 8 hours and 12 hours after the oral administration on the first day, and once or more in the morning and once or more in the afternoon from the second day through the 7th day. On the 7th day of administration, mice were sacrificed and anatomized to observe internal organs with the naked eye. Weight changes, according to the administration, were measured every day from the administration day. The results showed that the extracts and the compounds did not cause any specific clinical symptoms, weight change or death in mice. No change was observed in hematological tests, biochemical tests of blood and autopsy.

Therefore, the centipede extracts or a quinoline compound or a phenol compound isolated therefrom was evaluated to be safe substance since it did not cause any toxic change in mice up to the level of 1,000 mg/kg and its estimated $LD_{50}$ value is much greater than 1,000 mg/kg in mice.

The Manufacturing Examples of the composition for the present invention are described hereinafter.

Manufacturing Example 1

Preparation of Pharmaceutical Formulations

<1-1> Preparation of Powders

| | |
|---|---|
| Centipede extracts, quinoline compound or phenol compound | 2 g |
| Lactose | 1 g |

Powders were prepared by mixing all the above components and filled airtight bag with them.

<1-2> Preparation of Tablets

| | |
|---|---|
| Centipede extracts, quinoline compound or phenol compound | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Centipede extracts, quinoline compound or phenol | 100 mg |

| compound | |
|---|---|
| Corn starch | 100 mg |
| Lactose | 100 mg |
| Magnesium stearate | 2 mg |

Capsules were prepared by mixing the components above and filled gelatin capsules with them according to the conventional method for capsules.

<1-4> Preparation of Injectable Solutions

| | |
|---|---|
| Centipede extracts, quinoline compound or phenol compound | 10 μg/ml |
| Dilute hydrochloric acid BP | added until pH 3.5 |
| Sodium chloride injection BP | less than 1 ml |

The centipede extracts, a quinoline compound or a phenol compound was dissolved in sodium chloride injection BP and then the pH of the solution was adjusted to pH 3.5 using dilute hydrochloric acid BP. The volume of the solution was adjusted using sodium chloride injection BP. The solution was filled in 5 ml type 1 transparent glass ampoules, which were sealed by melting the glass. The ampoules were then sterilized by autoclaving at 120° C. for more than 15 minutes, resulting in the preparation of injectable solutions.

Manufacturing Example 2

Preparation of Food

Foodstuff containing the centipede extracts, a quinoline compound or a phenol compound of the present invention was prepared as follows.

<2-1> Preparation of Flour Food

Health improving flour food was prepared by adding the centipede extracts, a quinoline compound or a phenol compound of the present invention by 0.1~10.0 weight part to wheat flour and then making the flour into bread, cakes, cookies, crackers and noodles.

<2-2> Preparation of Soup and Gravies

The centipede extracts, a quinoline compound or a phenol compound of the present invention was added by 0.1~1.0 weight part to soup and gravies to prepare health improving meat products, noodle soups and gravies.

<2-3> Preparation of Ground Beef

The centipede extracts, a quinoline compound or a phenol compound of the present invention was added by 10 weight part to ground beef to prepare health improving ground beef.

<2-4> Preparation of Dairy Products

The centipede extracts, a quinoline compound or a phenol compound of the present invention was added by 0.1~1.0 weight part to milk to prepare health improving dairy products such as butter, ice cream, etc.

10<2-5> Preparation of Sunsik

Brown rice, barley, glutinous rice and coix (job's tear) were gelatinizated by the conventional method, followed by drying. The dried mixture was distributed and pulverized, resulting in 60-mesh size grain powders.

Black bean, black sesame and *perilla* were steamed and dried by the conventional method. The dried mixture was distributed and pulverized, resulting in 60-mesh size grain powders.

The centipede extracts, a quinoline compound or a phenol compound of the present invention was vacuum-concentrated under reduced pressure using a vacuum concentrator, which was then spray-dried with a hot-air drier. The dried material was pulverized by a grinder, resulting in 60-mesh size grain powders.

The prepared grain, seeds, and dried herbal mixture extract powders were all mixed at the following ratio.

Grain (brown rice 30 weight part, coix 15 weight part, barley 20 weight part),

Seeds (perilla 7 weight part, black bean 8 weight part, black sesame 7 weight part), Dried powder of the centipede extracts, quinoline compound or phenol compound of the present invention (1 weight part),

*Ganoderma lucidum* (0.5 weight part),

*Rehmannia glutinosa* (0.5 weight part)

Manufacturing Example 3

Preparation of Beverages

Beverages containing the centipede extracts, a quinoline compound or a phenol compound of the present invention were prepared as follows.

<3-1> Preparation of Health Beverages

Acid fructose (0.5%), oligosaccharide (2%), sugar (2%), salt (0.5%) and water (75%) were all mixed with the centipede extracts, a quinoline compound or a phenol compound of the present invention evenly, followed by sterilization. The mixture was put in a small container such as a glass bottle or pat bottle, resulting in health beverages.

<3-2> Preparation of Vegetable Juice 0.5 g of the centipede extracts, a quinoline compound or a phenol compound of the present invention was added to 1,000 ml of tomato or carrot juice to prepare health vegetable juice.

<3-3> Preparation of Fruit Juice 0.1 g of the centipede extracts, a quinoline compound or a phenol compound of the present invention was added to 1,000 ml of apple or grape juice to produce health fruit juice.

Industrial Applicability

As described hereinbefore, the novel quinoline compound, the centipede extracts and a quinoline compound and a phenol compound isolated from the extracts have excellent LDL-antioxidant activity, ACAT inhibiting activity, and anti-inflammatory activity as well but do not exhibit acute toxicity in mice.

Therefore, the composition of the present invention can be effectively used for the prevention and treatment of cardiovascular diseases including hyperlipidemia, atherosclerosis, coronary heart disease, and myocardial infarction mediated by LDL-oxidation or cholesteryl ester synthesis and accumulation.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An isolated quinoline compound represented by the following Formula 1

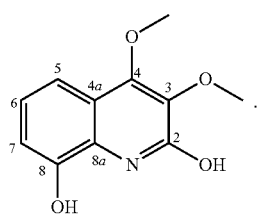

2. A composition comprising the compound represented by Formula 1 according to claim 1, and a pharmaceutically acceptable carrier.

3. The composition according to claim 2, wherein the pharmaceutical carrier is a foodstuff.

4. The composition according to claim 2, wherein the pharmaceutical carrier is a beverage.

5. The composition of claim 2, wherein the composition consists essentially of the compound of Formula 1 and the pharmaceutically acceptable carrier.

6. A preparation method of the quinoline compound of claim 1 comprising the following steps:
preparing centipede extracts from dried centipede by using a solvent;
preparing a chloroform-soluble phase from the above extracts suspended in water by serial fractionating with n-hexane, chloroform and ethylacetate; and
preparing the quinoline compound by isolating and purifying the chloroform-soluble phase with column chromatography.

7. The preparation method according to claim 6, wherein the solvent is selected from a group consisting of water, C1~C6 alcohol, C5~C7 alkane, chloroform, ethyl acetate, acetone, ether, benzene, methylene chloride, cyclohexane, petroleum ether or a mixture thereof.

8. The preparation method according to claim 6, wherein a mobile phage used in the step of separating and purifying fractions from chloroform-soluble phase by column chromatography is selected from a group consisting of water, chloroform, methanol or a mixture thereof.

* * * * *